United States Patent
Mowry et al.

[11] Patent Number: 5,922,106
[45] Date of Patent: Jul. 13, 1999

[54] AUTOMATED GAS CHROMATOGRAPHY

[75] Inventors: Curtis D. Mowry; Dianna S. Blair; Philip J. Rodacy, all of Albuquerque; Stephen D. Reber, Corrales, all of N.Mex.

[73] Assignee: Sandia Corporation, Albuquerque, N.Mex.

[21] Appl. No.: 09/063,234

[22] Filed: Apr. 20, 1998

[51] Int. Cl.[6] .................................................. B01D 15/08
[52] U.S. Cl. ........................... 95/87; 73/23.36; 73/23.41; 96/102; 96/105
[58] Field of Search ................ 73/23.35, 23.36, 73/23.37, 23.41, 23.42; 95/82, 87, 89; 96/101–106

[56] References Cited

U.S. PATENT DOCUMENTS

| | | | |
|---|---|---|---|
| 4,180,389 | 12/1979 | Paul | 96/101 X |
| 4,215,563 | 8/1980 | Clardy et al. | 73/23.35 |
| 4,932,272 | 6/1990 | Hogg | 73/23.35 X |
| 5,435,169 | 7/1995 | Mitra | 73/23.41 |
| 5,492,555 | 2/1996 | Strunk et al. | 96/106 X |
| 5,522,988 | 6/1996 | Cortes et al. | 210/198.2 |
| 5,686,656 | 11/1997 | Amirav et al. | 73/23.41 |
| 5,827,945 | 10/1998 | Arnold | 96/105 X |

OTHER PUBLICATIONS

Filippini, et al., "On–line capillary gas chromatography with automated liquid sampling, a powerful tool in biotechnology,"Analytica Chimica Acta, 255, 91–96, 1991.

*Primary Examiner*—Robert Spitzer
*Attorney, Agent, or Firm*—Elmer A. Klavetter

[57] ABSTRACT

An apparatus and process for the continuous, near real-time monitoring of low-level concentrations of organic compounds in a liquid, and, more particularly, a water stream. A small liquid volume of flow from a liquid process stream containing organic compounds is diverted by an automated process to a heated vaporization capillary where the liquid volume is vaporized to a gas that flows to an automated gas chromatograph separation column to chromatographically separate the organic compounds. Organic compounds are detected and the information transmitted to a control system for use in process control. Concentrations of organic compounds less than one part per million are detected in less than one minute.

16 Claims, 6 Drawing Sheets

AUTOMATED GAS CHROMATOGRAPHY

This invention was made with Government support under Contract No. DE-AC04-94AL85000 awarded by the Department of Energy. The Government has certain rights in the invention.

BACKGROUND OF THE INVENTION

The present invention relates to the field of gas chromatography. More particularly, the present invention relates to a method and apparatus for automatically analyzing organic elements of a sample from a continuously flowing liquid stream. In one aspect, the present invention relates to an on-line or automated gas chromatographic system for analyzing trace polar organic contaminants in a water process stream for use in electronics and semiconductor manufacturing operations.

Generally, when various solutions which are used in the manufacturing processes of many diverse industrial fields are to be subjected to an ingredient analysis for the purpose of quality or process control, the particular solution is sampled, and carried to the place where the analyzing apparatus is located. This analysis can be time-consuming and insufficiently responsive to provide timely information to control the process stream. Alternatively, on-line analysis of the chemical composition of one or more solutes in a carrier medium (e.g., a solvent) may be accomplished. A number of different analysis techniques can be utilized, including gas chromatography, to determine the nature of solutes in the process stream.

For example, in the manufacturing of semiconductor devices, ultra-pure water is used as a cleaning solvent. Organic contamination of this water, which occurs during routine operations such as wafer rinsing, affects the ability of the manufacturer to reuse the water. Currently, due to insufficient on-line monitoring methods, this process water is commonly diverted to waste or large holding tanks until adequate chemical analysis can be performed. To conserve the resource and subsequently reduce operating costs, this water can be reused in the same process or recycled for other applications, such as industrial cooling. However, for these applications, adequate on-line monitoring methods must be available to identify contaminants that can upset processes or damage equipment. Rapid detection of contamination, generally at sub part per million by volume ($ppm_v$) or low part per billion by volume ($ppb_v$) levels, is essential to prevent a decrease in product yield. Commercially available process monitors based on oxidation-$CO_2$ or combustion-ion chromatography methods are limited to sampling times of greater than three minutes. These monitors measure "total organic carbon" and have low part per billion ($ppb_v$) detection limits, although they do not identify the individual analytes present.

Gas chromatography is one of the most popular methods for sample analysis. A gas chromatography apparatus includes a sample injector for sample thermal vaporization and transfer into a separation column, a separation column in a temperature-controlled oven and a suitable detector to record the amount and time of appearance of the analyzed compounds. The injected sample mixture, comprising a solvent with a number of solutes, is separated in time and each solute is identified by its time of elution. The time of elution for each solute is a characteristic of its chemical and physical properties relative to the solvent and other solutes.

To detect and analyze volatile organic compounds, the compounds are typically extracted from aqueous solutions by bubbling a sparging gas through the liquid. The analyte comes to an equilibrium concentration in the sparging gas, and the gas is then analyzed using gas chromatography. Sparging is a process by which volatiles are extracted from water by bubbling a clean gas through the water; however, this process generally takes several minutes. The sparging gas then flows through the gas chromatographic injection system for separation via a separation column (e.g., a capillary column) and a detection device. The separation column operation can be optimized for the individual constituents that are to be detected by varying the column temperature, type, and physical characteristics. The overall analysis time ranges from approximately 10 to 20 minutes, depending on the nature of the constituents to be detected.

Generally, samples are introduced into the gas chromatograph (GC) through injection from a small syringe that penetrates a septum and dispenses a measured amount of liquid sample into the GC injector for vaporization and further transport by a carrier gas into a separation column. The effluent from the separation column is passed through a detection device. Typical GC detectors include a flame ionization detector (FID), a flame photometric detector (FPD), a thermionic detector (TID), a thermal conductivity detector (TCD), an electron captive detector (ECD), a mass spectrometer (MS), or a Fourier transform infrared spectrometer (FTIR).

The effectiveness of a GC to detect particular solutes depends on the relative characteristics of the solutes to the carrier solvent as well as the characteristics of the GC separation column and detector. In general, solutes that are closely related by chemical characteristics to the solvent are more difficult to separate and generally require longer analysis times. For example, polar solutes with water as the solvent are difficult to separate because the solutes may be extremely soluble in the polar water solvent. In semiconductor process operations, such polar solutes consist of such compounds as methyl ethyl ketone (MEK), isopropanol (IPA), acetone, p-xylene, butyl acetate, ethyl benzene, ethylene glycol, and 2-ethoxyethyl acetate. A typical separation column can be several tens of meters in length, requiring minutes of transport time for the sample to pass through the column and detector.

Current methods for preconcentration of the solutes to be analyzed by gas chromatography analysis include membrane separation, sorbent trapping or extraction, cryo-trapping, and liquid—liquid extraction. All of these preconcentration methods significantly increase the time of analysis, generally requiring several to tens of minutes. Mitra (U.S. Pat. No. 5,435,169, issued on Jul. 25, 1995) discloses a method and device for continuous monitoring of low level concentrations of volatile organic compounds in waste water streams, where the fluid stream passes through an on-line micro sorbent trap to concentrate the organic compounds. This sorbent trap contains the sample for a period of time before releasing it as a desorption pulse for subsequent contaminant monitoring. The sorbent trap is designed to retain and concentrate the analytes of interest; therefore, the trap must have an adsorbent specific to the analytes of interest that will not react with the solvent. Amirav et al. (U.S. Pat. No. 5,686,656, issued on Nov. 11, 1997) describe a method and device for introducing liquid samples into a gas chromatograph, particularly samples containing biological compounds. The method, however, requires several minutes for analysis and does not allow for on-line and continuous sample analysis.

Direct injection methods, which use an automated valve to sample and inject a portion of the liquid stream into a gas chromatograph, have the potential to be much faster. The sampling rate of automated systems is dependent only upon the time required for analyte separation in the chromatographic column. Due to the high volumetric flow rates commonly encountered in process-streams, rapid sampling and analysis rates improve the accuracy of the chemical contaminant information and the ability to define the actual volume of the process water being analyzed.

Filippini et al. (Analytica Chimica Acta, 255, 91–96, 1991) describe an analysis method for on-line capillary gas chromatography with automated liquid sampling using a liquid sample injection valve that vaporizes the liquid sample by means of a heated carrier gas. In Filippini et al., the injection valve is attached to the commercial gas chromatograph, which must be heated to high temperature (220° C.), as this is where the vaporization of the liquid occurs. This causes injection variability due to potential bubble formation in the metering groove, as well as buildup of non-volatile contaminants within the metering groove.

Cortes et al. (U.S. Pat. No. 5,522,988 issued on Jun. 4, 1996) describes an on-line coupled liquid chromatography and gas chromatography apparatus. The apparatus includes a vaporizing chamber that is interposed between a liquid chromatographic column and a capillary gas chromatographic column. Because of the use of liquid chromatography, the input stream to the liquid chromatographic column cannot be completely aqueous. Additionally, the analysis requires at least several minutes to complete.

In spite of the above, sampling and analysis of industrial water recycling, wastewater, or process streams present many challenges. For many water recycling and wastewater processes, particularly water process streams used in the electronics and semiconductor industries, the stream must be sampled on line and in a continuous or near-continuous manner. The analysis must be rapid to minimize potential subsequent contamination downstream. The analysis must also be able to detect low concentrations, generally at sub part per million levels, of organic contaminants.

The automated, aqueous, gas chromatographic system of the present invention solves many problems encountered in traditional recycling stream analysis. Typically, the recycling/process stream is sampled periodically, followed by off-line analysis. The present invention, relative to off-line analysis, decreases the chance of human error, eliminates the need for external handling and therefore the possibility of external contamination, and significantly reduces the time required for analysis. Existing systems employ holding tanks to temporarily store effluent while off-line analysis is performed, at which time the tank contents are then sent to waste or back into the process stream. Also, a low-volume contamination event can flow into a (potentially uncontaminated) holding tank, resulting in a much larger volume that must then be sent to waste. The automated on-line stream analysis apparatus and method of the present invention allows the divert decision to be made rapidly and automatically, eliminating the need for holding tanks and human supervision. This increases the efficiency of the recycle process, reduces waste production and the labor required, all of which reduce the costs associated with process stream recycling. Efficient recycling is of great importance, for example, in the semiconductor industry, which uses highly purified water in many processes. Purifying the water is initially costly, and re-use of impure recycled water can result in product loss and production downtime.

Ideally, process streams must be monitored continuously, reliably, inexpensively, and with minimum supervision. The present invention utilizes inexpensive, rugged parts already commercially available and allows measurements to be made in less than one minute. The unit is fully automated, requires little supervision, and performs alarm functions under user-defined conditions of contaminant detection.

The present invention has several advantages relative to existing on-line gas chromatographic technologies. No analyte sparging is required and, except for the brief sampling time, carrier gas flows continuously through the same valve that introduces the sample. The vaporization column connects directly to the valve and only a small aliquot sample is taken from the process stream. Common auto-sampler or auto-injector parts such as needle, septum, and glass injection liner have been eliminated and each sub-system is entirely isothermal. The present invention provides a system to control the process stream and allow decisions to be made to divert the liquid in the process stream to waste in near real-time, eliminating the need and therefore cost for holding tanks required for storage while waiting for off-line analysis.

Relative to on-line "total organic carbon" (TOC) analyzers, the present invention has a much shorter response time, one minute or less for common polar hydrocarbons. This allows contamination events to be defined more precisely, in turn preventing waste of uncontaminated water and reducing the spread of the contaminant. Because TOC analyzers add chemical reagents to the water, requiring that the flow to the instrument be sent to waste without fail, the present invention uses a smaller aliquot, and consumes the sample during analysis. For the present invention, wastewater is only created during a calibration event. TOC analyzers give a single measurement value, whereas the present invention allows the user to quantify and identify individual contaminants. This information may allow the user to determine the source or location of the process anomaly, which is not possible using a TOC analyzer. The present invention also has the flexibility to be customized for a particular contaminant or group of contaminants. Different column coatings, commercially available, can be interchanged to customize the instrument.

SUMMARY OF THE INVENTION

The invention comprises an apparatus and method for the continuous, near real-time monitoring of low-level concentrations of polar and non-polar organic compounds in a liquid, and more particularly, a water, stream.

One aspect of the invention is an automated gas chromatographic apparatus for analyzing organic compounds in a liquid process stream containing a liquid solvent and solute ingredients, comprising means for continuously diverting a portion of a liquid process stream to the automated gas chromatograph; means for maintaining the diverted portion of the liquid process stream at an approximately constant temperature; means for periodically sampling a liquid volume of the diverted liquid process stream; a continuously flowing carrier gas stream wherein the carrier gas stream directs the liquid volume into a heated vaporization capillary; an analytic separation column; and a detector.

The invention is also an automated gas chromatographic method for analyzing organic compounds in a liquid process stream containing a liquid solvent and solute ingredients, comprising continuously diverting a portion of a liquid process stream to the automated gas chromatograph; maintaining the diverted portion of the liquid process stream at an approximately constant temperature; periodically sampling a liquid volume of the diverted liquid process stream; directing the sampled liquid volume by means of a continuously flowing carrier gas into a heated vaporization capillary; vaporizing the sampled liquid volume; separating the solute ingredients; and detecting the solute ingredients.

In the method of the invention, concentrations of organic compounds less than one part per million are detected in less than one minute after sampling the liquid process stream.

The invention is also a method wherein the liquid process stream is water and the solute ingredients are selected from the group consisting essentially of methyl ethyl ketone, isopropanol, acetone, xylenes, butyl acetate, ethyl benzene, ethylene glycol, and 2-ethoxyethyl acetate.

BRIEF DESCRIPTIONS OF THE DRAWINGS

FIG. 2 shows a) a schematic of one embodiment of the present invention, b) valve in its calibration position and c) valve in its test position.

DETAILED DESCRIPTION OF THE INVENTION

The present invention comprises an apparatus and process for the continuous, near real-time monitoring of very low-level concentrations of polar and non-polar organic compounds in a liquid, and more particularly, a water, stream. The apparatus comprises a means to divert flow from a liquid process stream containing organic compounds to a means by which a small liquid volume of that flow is sampled, a heated vaporization capillary wherein the liquid volume is vaporized to a gas, a separation column to chromatographically separate the organic compounds, a detector, and means to control the apparatus.

Figure 1:
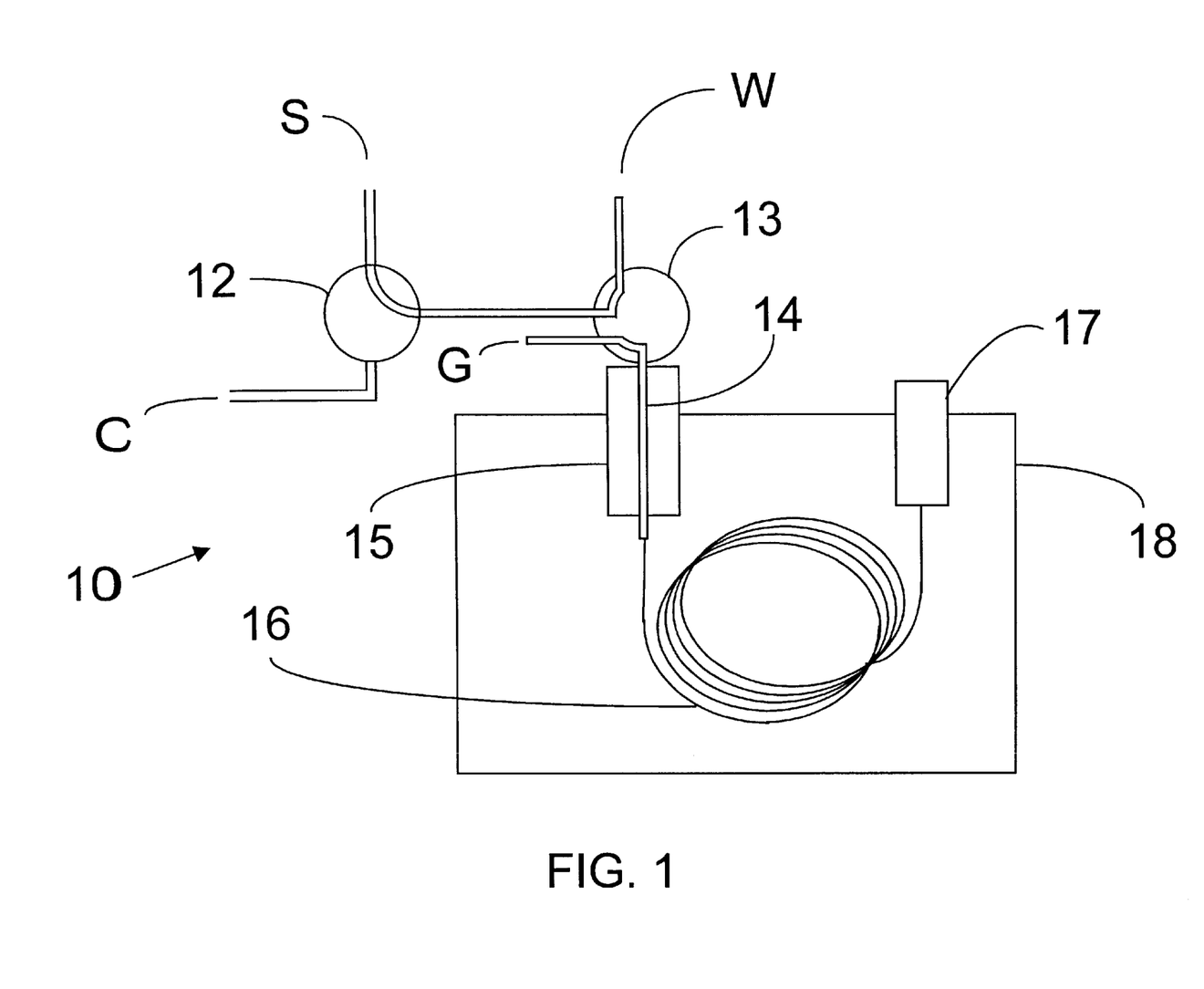
FIG. 1 shows a schematic of the general on-line, aqueous-analysis, gas chromatographic system.

Referring to FIG. 1, the apparatus according to the present invention, an automated gas chromatography system 10, is shown. The apparatus includes a multi-port valve 12 with at least three ports, wherein one port is an inlet to divert flow from a liquid process stream S, another port is used as an inlet for a calibration solution C and a third port is the outlet to a multi-port valve 13. Valve 12 directs either flow from the liquid process stream S or the calibration solution C to valve 13. Valve 13 has at least four ports and is kept at a constant temperature, for example, by heat tape, insulation, and a controller (not shown). One port is the inlet from valve 12, another port is an inlet for a continuously flowing carrier gas G, another port is an outlet for that portion of the flow from the liquid process stream that is not sampled and is connected to outlet line W and another port is an outlet for the liquid aliquot of the flow that is sampled and is connected to the vaporization capillary 14. The vaporization capillary 14 is kept heated to a constant elevated temperature by a transfer heater 15. The vaporization capillary 14 is connected to an analytical separation column 16 inside of a temperature-controlled oven 18, such as a gas chromatographic oven. The analytical separation column 16 is connected to a detector 17, such as a flame ionization detector (FID), a flame photometric detector (FPD), a thermionic detector (TID), a thermal conductivity detector (TCD), an electron captive detector (ECD), a mass spectrometer (MS), or a Fourier transform infrared spectrometer (FTIR), and preferably an FID.

Figure 2A:
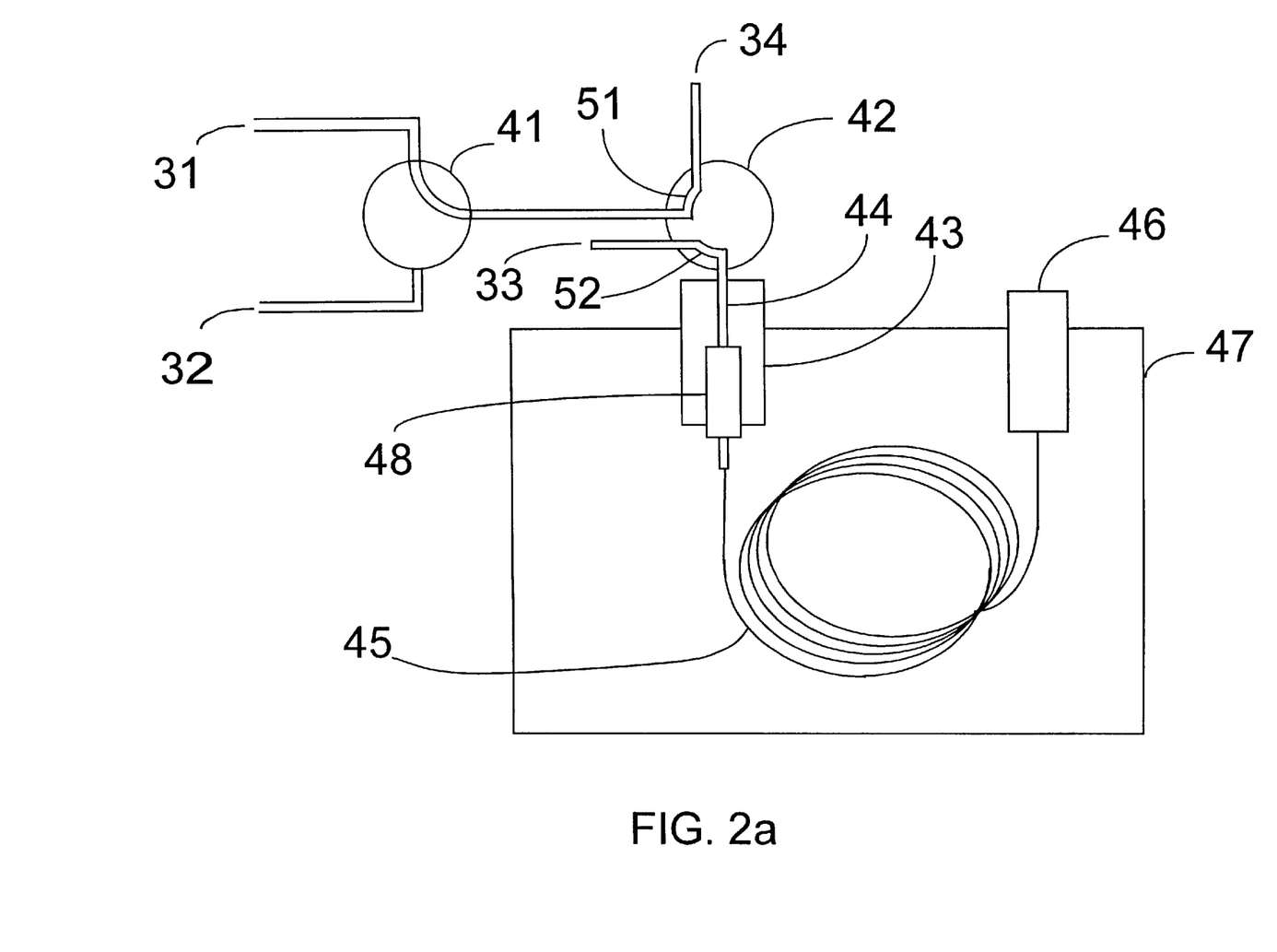
Figure 2B:
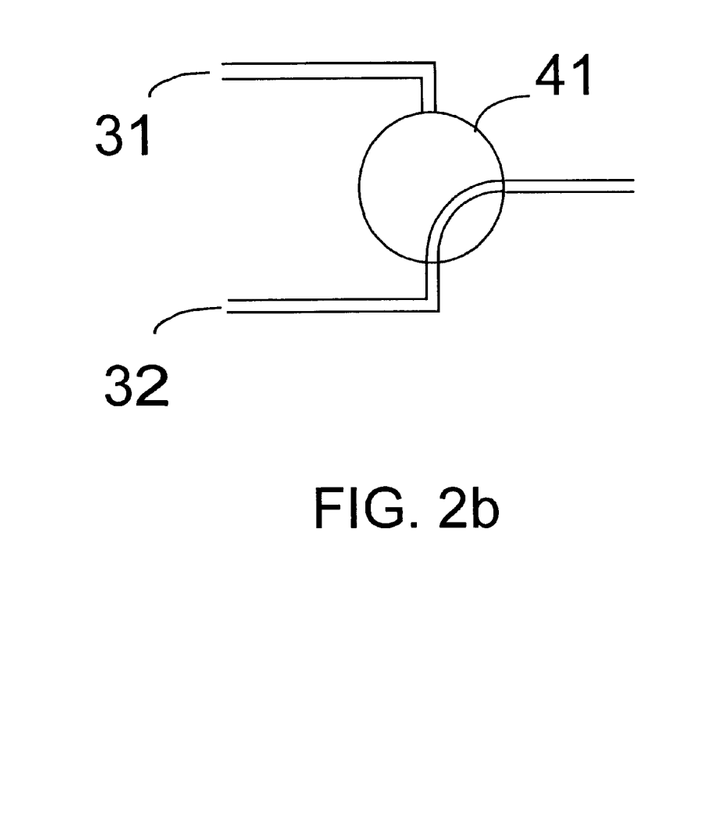
Figure 2C:
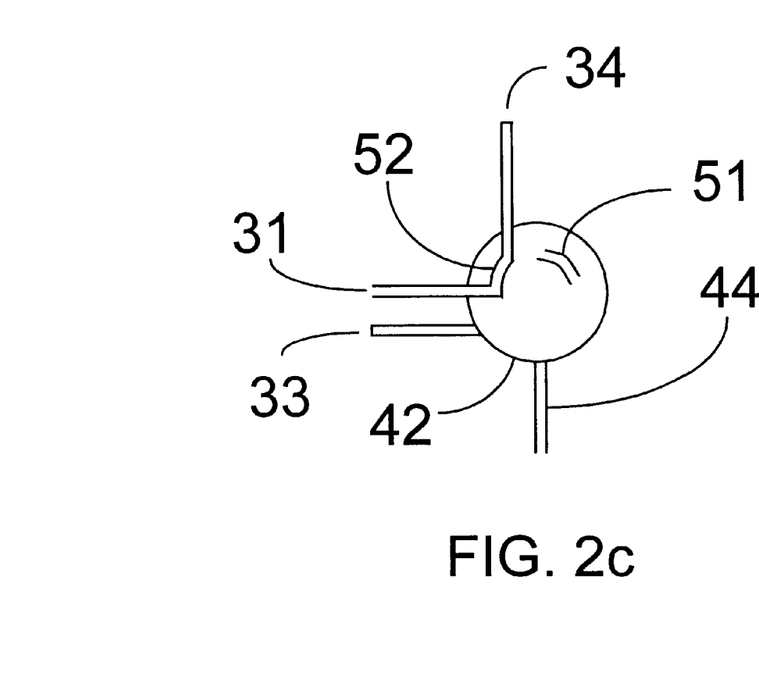

In one embodiment, shown in FIG. 2a, an aqueous process stream 31, containing low concentrations of polar organic compounds, flows through valve 41, a three-port pneumatic valve with a single internal loop, to valve 42. The flow rate used in this embodiment was approximately 10 cc/min. When valve 41 is in its normal position, as depicted in FIG. 2a, liquid flow from the aqueous process stream 31 flows through valve 41. When valve 41 is in its calibration position, as depicted in FIG. 2b, a calibration solution 32 flows through valve 41 to valve 42, as discussed below. Valve 42 is a four-port pneumatic valve, Valco Instruments, Houston, Tex., model A2C14WF.5 in this embodiment. When valve 42 is in its normal position, the aqueous process stream 31 flows through valve 42 and is returned to the process stream or other designated stream via conduit 34, as depicted in FIG. 2a. Additionally, the carrier gas stream 33 flows continuously through one port of valve 42 to the vaporization column 44, as will be discussed more fully below. As depicted in FIG. 2a, when valve 42 is in its normal position, loop 51 is positioned to return the process stream 31 to conduit 34 and sampling groove 52 is positioned for the carrier gas stream 33 to flow to the vaporization column 44. Alternatively, when valve 41 is in its normal position, as depicted in FIG. 2a and valve 42 is in its test position, as depicted in FIG. 2c, the aqueous process stream 31 flows into the sampling groove 52, positioned as depicted in FIG. 2c, to collect a liquid aliquot of approximately 0.5–1.0 microliters. After approximately 6 seconds, valve 42 is returned to its normal position in FIG. 2a, and the carrier gas stream 33 (e.g., helium), flowing at a rate of approximately 15 cc/min, introduces the collected liquid aliquot from sampling groove 52 into the heated vaporization capillary 44.

The vaporization capillary 44 is heated by a transfer heater, consisting of a heated metal block 43 and the gas chromatographic injection heater 48 in the present embodiment. The vaporization capillary 44 connects directly to the valve 42 and to an analytical separation column 45, such as a Supelco, Bellafonte, Pa., Supelco Wax column, 0.5 $\mu$m film thickness, 0.32 mm i.d., in the interior of a temperature-controlled gas chromatography (GC) oven 47, a Varian Instruments, San Fernando, Calif., model 3600 in this embodiment. The separation column 45 is connected to a flame ionization detector 46, which provides an output signal to a means (not shown) for collecting and analyzing the data obtained from the detector.

Analog data is collected from the detector and processed using a commercial analog-to-digital converter (not shown), such as Perkin Elmer Corp., San Jose, Calif., model 900 and software, such as Perkin Elmer Corp., San Jose, Calif., Turbochrom version 4.1, designed for gas chromatography. The software can perform a variety of functions from self-calibration to integration. This software allows the gas chromatographic system of the present invention to operate for greater than 24 hours without supervision. Custom software processes data collected by the commercial software and performs alarm functions. For example, if a specific analyte is detected above a certain threshold, an alarm will sound and the time and nature of the event is saved in a log file. Depending upon the utilization of the system, the alarm is used to trigger a process-line valve or other control device. An electronic relay (not shown) controls the positioning of pneumatic valve 42 in FIG. 2a. The analog-to-digital converter supplies the signal to initiate analysis and controls the timing and position of pneumatic valve 41 in FIG. 2a.

A calibration solution 32 is periodically analyzed, as standard in the art, to aid in solute identification and quantification. The calibration solution 32, composed of the solvent and solutes of interest, flows through valve 41 to valve 42, where the calibration solution 32 is sampled by positioning valve 42 in its sampling or test position, as depicted in FIG. 2c to collect a liquid aliquot of the calibration solution 32 of approximately 0.5–1 microliters. Similarly to the process described above, after approximately 6 seconds, valve 42 is returned to its normal position in FIG. 2a, and the carrier gas stream 33 (e.g., helium), flowing at a rate of approximately 15 cc/min, introduces the collected liquid aliquot into the heated vaporization capillary 44. The liquid aliquot is vaporized, separated by the analytical separation column 45 and detected by the detector 46 to provide calibration information on the solutes in the calibration solution 32.

In operation, analysis of low concentrations of organic compounds in a liquid process stream is performed by continuously diverting all, or a fraction of, the liquid process stream, periodically sampling a volume of the diverted liquid process stream, directing the sampled volume by means of a continuously flowing carrier gas into a heated vaporization capillary, vaporizing the sampled volume into a gas, separating the compounds and detecting the compounds. The system and analysis is automated using conventional control electronics and software.

In one embodiment of the analysis method, as depicted in FIG. 2a, an aqueous stream 31 at a flow rate of approximately 10 cc/min, containing low concentrations of methyl ethyl ketone (MEK) and isopropanol (IPA), flows into valve 41, a three-port, pneumatic valve that has a single internal loop of 1/16" diameter and directs either calibration solution flow 32 or sample flow 31 to pneumatic valve 42. The flow rate used in this embodiment was approximately 10 cc/min. When valve 41 is in its normal position, as depicted in FIG. 2a, liquid flow from the aqueous process stream 31 flows through valve 41.

Figure 3:
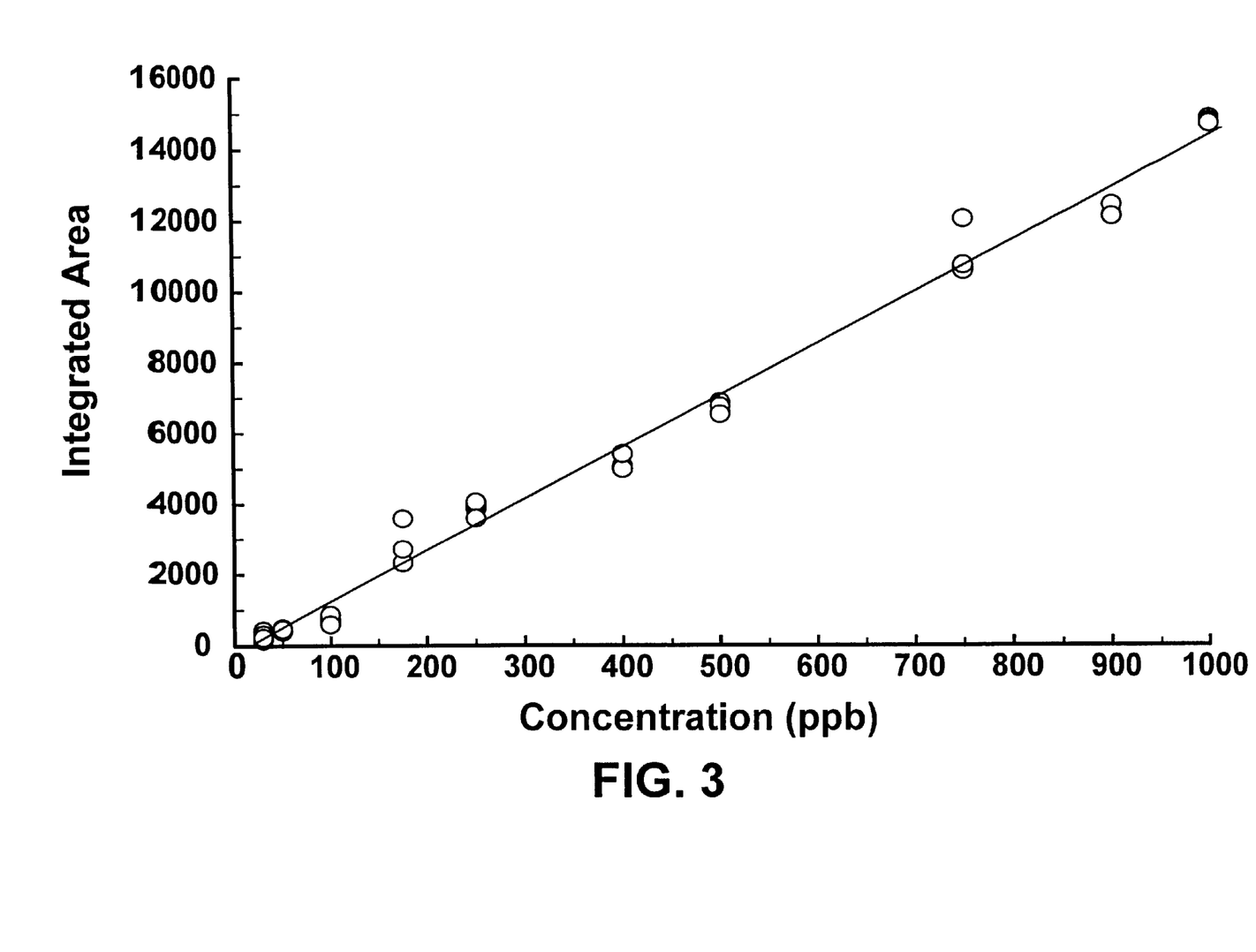
FIG. 3 shows a sample calibration curve.

When valve 41 is in its calibration position, as depicted in FIG. 2b, a calibration solution 32 flows through valve 41 to valve 42, where valve 42 is in the test or injection position depicted in FIG. 2c, to provide calibration data to quantify the concentrations of the organic compounds to be detected. FIG. 3 shows a calibration curve for acetone. All analytes exhibited linear calibration curves. Linear calibration was expected using flame ionization detection; however, this data demonstrates that the inlet system performed as designed under contaminant concentrations from 50 ppb to 1 ppm.

Valve 42 is a four-port pneumatic valve, Valco Instruments, Houston, Tex., model A2C14WF.5 in this embodiment, kept at an approximately constant 150° C. using either a valve heater or resistive heat tape, a thermocouple, and temperature controller. The valve area is insulated. Pneumatic valve 42 has two internal loops; a 0.5 microliter sampling groove 52 and a 1/16" diameter loop 51. When valve 42 is in its normal position, the aqueous process stream 31 flows through valve 42 and is returned to the process stream or other designated stream via conduit 34, as depicted in FIG. 2a. Additionally, the carrier gas stream 33, helium, flows continuously through one port of valve 42 to the vaporization column 44, at a flow rate of approximately 15 cc/min. As depicted in FIG. 2a, when valve 42 is in its normal position, loop 51 is positioned to return the process stream 31 to conduit 34 and sampling groove 52 is positioned for the carrier gas stream 33 to flow to the vaporization column 44. To initiate analysis of the aqueous process stream, valve 41 is in its normal position, as depicted in FIG. 2a and valve 42 is rotated to its test position, as depicted in FIG. 2c so that the aqueous process stream 31 flows into the sampling groove 52, positioned as depicted in FIG. 2c, to collect a liquid aliquot of approximately 0.5–1.0 microliters. After approximately 6 seconds, valve 42 is returned to its normal position in FIG. 2a, and the helium carrier gas stream 33, introduces the collected liquid aliquot into the heated vaporization capillary 44.

The vaporization capillary 44 is heated by a transfer heater, consisting of a heated aluminum block 43 and the gas chromatographic injection heater 48 in the present embodiment, to a constant temperature of approximately 250° C. The aluminum block is kept at the elevated temperature by a temperature controller using a cartridge heater and thermocouple. The vaporization capillary 44 is uncoated fused silica, 0.53 mm I.D., 25 cm long and connects directly to the pneumatic valve 42 and to an analytical separation column 45 in the interior of the GC oven 47. The vaporization capillary 44 may be a hollow cylinder made of any material inert to the solvent and solutes in the liquid stream being sampled. There it rapidly vaporizes so that it is introduced as a gas or vapor to the analytical separation column 45, which was a Supelco, Bellafonte, Pa., Supelco Wax column of 0.5 μm film thickness, 0.32 mm i.d. in this embodiment. If other liquid streams and solutes are being analyzed, the analytic separation column can be changed according to well-known gas chromatographic techniques. For example, the column may be a capillary, large-bore or packed column and may be of different diameter and length. The GC oven 47 is maintained at 50° C., and detection is achieved with a flame ionization detector 46. The FID detector requires both hydrogen gas and air for operation. FID is used in this application because the water solvent does not affect its detection capability. Other detectors could be used for other solvents and solutes of interest.

Gas chromatographic analysis of water samples with trace (parts-per-billion) contaminant levels of methyl ethyl ketone (MEK) and isopropanol (IPA) was achieved in less than one minute analysis time using flame ionization detection, while still providing chromatographic separation for most analytes studied. The system configuration, which includes a short column, high carrier flow rates, isothermal operation, automated valves, and computer control, allows for rapid and automated detection at low parts-per-billion detection limits. The automated data post-processing methods demonstrate the ability to use this system as a stand alone process monitor.

Figure 4:
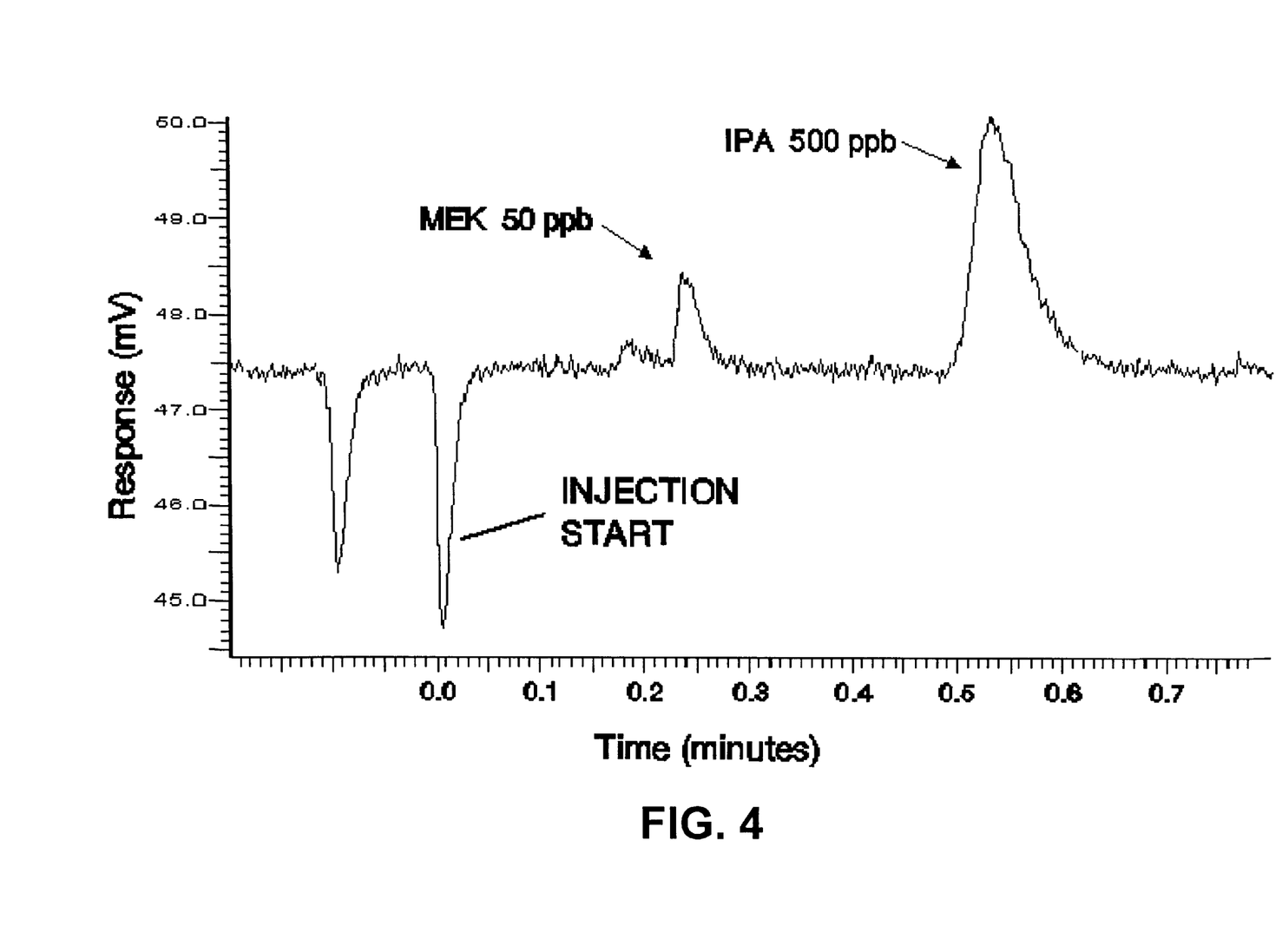
FIG. 4 shows an example chromatogram of polar contaminants in water.

An example chromatogram is shown in FIG. 4. Detector response is plotted versus time for an injection of an aqueous solution of MEK and IPA. The negative signal spikes early in the chromatogram result from the pressure drop caused by the actuation of valve 42. The results demonstrate the capability of the present invention to detect polar organic contaminants in water in less than one minute from the time of sample diversion to the invention by actuation of a valve through the detection analysis. The results also demonstrate the sensitivity of the detection limits of the present invention wherein methyl ethyl ketone and isopropanol are detected at sub $ppm_v$ concentrations.

Figure 5:
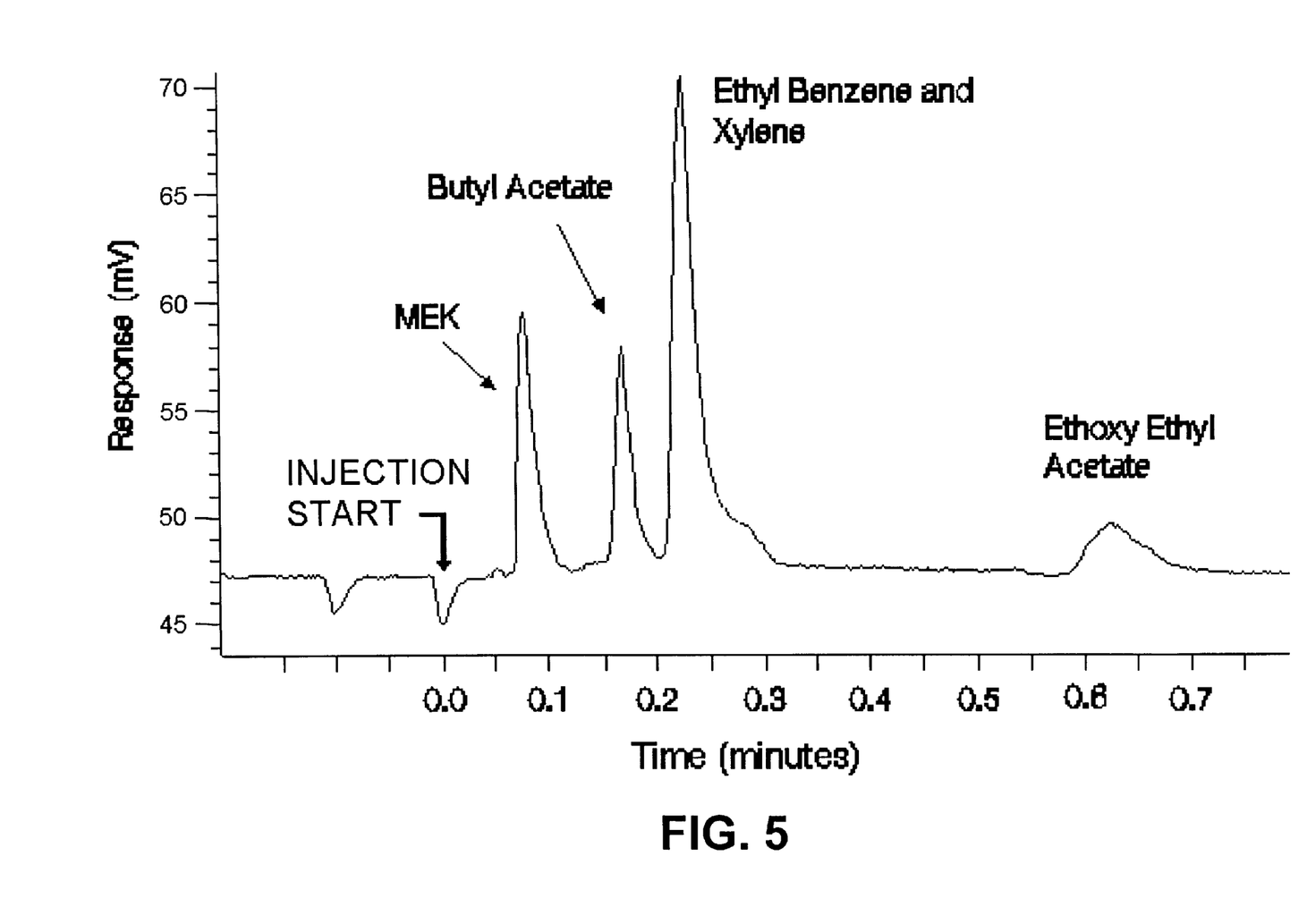
FIG. 5 shows an example chromatogram of a simulated waste stream.

Other analytes tested with simulated waste streams include acetone, p-xylene, butyl acetate, ethyl benzene, and 2-ethoxyethyl acetate. An example chromatogram of these analytes is shown in FIG. 5. Again, the results demonstrate the capability for rapid and sensitive detection of contaminants in water.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. An automated gas chromatographic method for analyzing organic compounds in a liquid process stream containing a liquid solvent and solute ingredients, comprising:
   continuously diverting a portion of a liquid process stream to a gas chromatograph;
   periodically sampling a liquid volume of the diverted liquid process stream;
   directing the sampled liquid volume by means of a continuously flowing carrier gas into a heated vaporization capillary;
   vaporizing the sampled liquid volume;
   separating the solute ingredients; and
   detecting the solute ingredients.

2. The method of claim 1, wherein said detecting occurs in less than approximately one minute after sampling the liquid volume of the diverted liquid process stream.

3. The method of claim 1, wherein said liquid process stream is aqueous.

4. The method of claim 1, wherein said solute ingredients are selected from the group consisting essentially of methyl ethyl ketone, isopropanol, acetone, xylenes, butyl acetate, ethyl benzene, ethylene glycol, and 2-ethoxyethyl acetate, or a mixture thereof.

5. The method of claim 1, wherein the sampled liquid volume is maintained at an approximately constant temperature prior to being directed into the heated vaporization capillary.

6. The method of claim 5, wherein the approximately constant temperature is approximately 150° C.

7. The method of claim 1, wherein the heated vaporization capillary is heated to a temperature of approximately 250° C.

8. The method of claim 1, wherein the carrier gas is helium.

9. The method of claim 1, wherein the sampled liquid volume is approximately 0.5–1.0 microliters.

10. The method of claim 1, wherein detecting the solute ingredients is accomplished by a detector selected from the group consisting of: a flame ionization detector, a flame photometric detector, a thermionic detector, a thermal conductivity detector, an electron captive detector, a mass spectrometer, or a Fourier transform infrared spectrometer.

11. An automated gas chromatographic apparatus for analyzing organic compounds in a liquid process stream containing a liquid solvent and solute ingredients, comprising:
    means for continuously diverting a portion of a liquid process stream to a gas chromatograph;
    means for periodically sampling a liquid volume of the diverted liquid process stream;
    a continuously flowing carrier gas stream wherein the carrier gas stream directs the sampled liquid volume into a heated vaporization capillary;
    an analytic separation column; and
    a detector.

12. The apparatus of claim 11, wherein the means to continuously divert a portion of a liquid process stream to the automated gas chromatograph is a multi-port pneumatic valve with at least three ports.

13. The apparatus of claim 11, wherein the means for periodically sampling a liquid volume of the diverted process stream is a multi-port pneumatic valve with at least four ports.

14. The apparatus of claim 11, wherein the vaporization capillary is fused silica.

15. The apparatus of claim 11, wherein the detector is selected from the group consisting of a flame ionization detector, a flame photometric detector, a thermionic detector, a thermal conductivity detector, an electron captive detector, a mass spectrometer, and Fourier transform infrared spectrometer.

16. The apparatus of claim 11, further comprising electronic means for controlling the means for periodically sampling a liquid volume of the diverted process stream.

* * * * *